(12) United States Patent
Karlsson et al.

(10) Patent No.: US 9,844,448 B2
(45) Date of Patent: *Dec. 19, 2017

(54) PROSTHETIC KNEE

(71) Applicant: OSSUR HF, Reykjavik (IS)

(72) Inventors: Sigurdur Gisli Karlsson, Kopavogur (IS); Sigurdur Hannesson, Kopavogur (IS); Sigurdur Olafsson, Reykjavik (IS)

(73) Assignee: OSSUR HF, Reykjavik (IS)

( * ) Notice: Subject to any disclaimer, the term of this patent is extended or adjusted under 35 U.S.C. 154(b) by 109 days.

This patent is subject to a terminal disclaimer.

(21) Appl. No.: 14/840,086

(22) Filed: Aug. 31, 2015

(65) Prior Publication Data

US 2015/0366679 A1 Dec. 24, 2015

Related U.S. Application Data

(63) Continuation of application No. 13/857,404, filed on Apr. 5, 2013, now Pat. No. 9,149,371.

(Continued)

(51) Int. Cl.
*A61F 2/64* (2006.01)
*A61F 2/80* (2006.01)
(Continued)

(52) U.S. Cl.
CPC ............... *A61F 2/644* (2013.01); *A61F 2/64* (2013.01); *A61F 2/68* (2013.01); *A61F 2/80* (2013.01);
(Continued)

(58) Field of Classification Search
CPC .......... A61F 2/642; A61F 2/644; A61F 2/646; A61F 2002/6854; A61F 2002/6818
See application file for complete search history.

(56) References Cited

U.S. PATENT DOCUMENTS 3,533,651 A 10/1970 Prahl
3,663,967 A 5/1972 Vermillion
(Continued)

FOREIGN PATENT DOCUMENTS

DE 20 2005 019 125 U1 10/2007
GB 2 004 753 A 4/1979
(Continued)

OTHER PUBLICATIONS

Product Brochure: Total Knee System Adjustment, Dec. 1, 2008, 2 pages, www.ossur.com.
(Continued)

*Primary Examiner* — David H Willse
(74) *Attorney, Agent, or Firm* — Workman Nydegger

(57) ABSTRACT

A prosthetic knee for active users has a locking head generally parallel to a vertical axis of the prosthetic knee, a chassis, and a plurality of links connecting the locking head to the chassis. The knee includes a swing control mechanism having a flexion stop connected to the chassis and arranged to control the flexion angle of the knee. The flexion stop extends outwardly from the chassis and obliquely relative to the vertical axis. The knee has an audible feedback mechanism for providing the user with information about the location of the knee. The knee may also have a block lock forming a manually activated mechanism allowing load bearing in a flexed position.

7 Claims, 11 Drawing Sheets

Related U.S. Application Data

(60) Provisional application No. 61/692,508, filed on Aug. 23, 2012, provisional application No. 61/620,592, filed on Apr. 5, 2012.

(51) Int. Cl.
| | |
|---|---|
| A61F 2/68 | (2006.01) |
| A61F 2/50 | (2006.01) |
| A61F 2/60 | (2006.01) |
| A61F 2/66 | (2006.01) |

(52) U.S. Cl.
CPC .......... *A61F 2/60* (2013.01); *A61F 2002/503* (2013.01); *A61F 2002/5006* (2013.01); *A61F 2002/5009* (2013.01); *A61F 2002/5018* (2013.01); *A61F 2002/5043* (2013.01); *A61F 2002/5072* (2013.01); *A61F 2002/5079* (2013.01); *A61F 2002/6678* (2013.01); *A61F 2002/689* (2013.01); *A61F 2002/6809* (2013.01); *A61F 2002/6818* (2013.01); *A61F 2002/6854* (2013.01)

(56) References Cited

U.S. PATENT DOCUMENTS

| | | |
|---|---|---|
| 3,666,299 A | 5/1972 | Butler |
| 3,823,424 A | 7/1974 | May |
| 3,837,010 A | 9/1974 | Prout |
| 4,005,496 A | 2/1977 | Wilkes |
| 4,023,215 A | 5/1977 | Moore |
| 4,034,419 A | 7/1977 | Roberts |
| 4,135,254 A | 1/1979 | Weber et al. |
| 4,145,766 A | 3/1979 | May |
| 4,685,926 A | 8/1987 | Haupt |
| 4,911,709 A | 3/1990 | Marlow et al. |
| 5,314,498 A | 5/1994 | Gramnas |
| 5,704,946 A | 1/1998 | Greene |
| 5,728,172 A | 3/1998 | Krieger |
| 5,728,173 A | 3/1998 | Chen |
| 5,746,774 A | 5/1998 | Kramer et al. |
| 5,800,566 A | 9/1998 | Gramnas |
| 5,911,709 A | 6/1999 | Hogan |
| 5,921,358 A | 7/1999 | Gramnas |
| 6,086,616 A | 7/2000 | Okuda et al. |
| D439,339 S | 3/2001 | Sawatzki |
| D446,304 S | 8/2001 | Sawatzki et al. |
| 6,471,664 B1 | 10/2002 | Campbell et al. |
| 6,508,843 B2 | 1/2003 | Suzuki |
| 6,706,074 B1 | 3/2004 | Chen |
| 6,752,835 B2 | 6/2004 | Shen |
| 6,764,244 B2 | 7/2004 | Pansiera |
| 6,911,051 B2 | 6/2005 | Cheng |
| D522,142 S | 5/2006 | Boiten |
| D523,959 S | 6/2006 | Muehlenberend |
| 7,066,964 B2 | 6/2006 | Wild |
| D525,709 S | 7/2006 | Boiten |
| D526,062 S | 8/2006 | Harn et al. |
| D526,412 S | 8/2006 | Harn et al. |
| D527,458 S | 8/2006 | Harn et al. |
| 7,087,091 B1 | 8/2006 | Chen |
| 7,147,667 B2 | 12/2006 | Bedard |
| 7,195,647 B2 | 3/2007 | Chen et al. |
| D553,741 S | 10/2007 | Chen |
| 7,438,843 B2 | 10/2008 | Asgeirsson |
| D592,749 S | 5/2009 | Muhlenberend |
| 7,582,119 B2 | 9/2009 | Chen |
| 7,618,463 B2 | 11/2009 | Oddsson et al. |
| 7,685,926 B2 | 3/2010 | Mori |
| 7,833,285 B2 | 11/2010 | Reinhardt |
| 7,833,286 B2 | 11/2010 | Slemker |
| D632,790 S | 2/2011 | Cheng |
| 8,202,325 B2 | 6/2012 | Albrecht-Laatsch et al. |
| 8,764,849 B2 | 7/2014 | Omarsson et al. |
| 9,149,371 B2 * | 10/2015 | Karlsson ................ A61F 2/644 |
| 2002/0026246 A1 | 2/2002 | Suzuki |
| 2002/0188355 A1 | 12/2002 | Chen |
| 2006/0259153 A1 | 11/2006 | Harn et al. |
| 2008/0281427 A1 | 11/2008 | Shen |
| 2009/0030530 A1 | 1/2009 | Martin |
| 2009/0143869 A1 | 6/2009 | Cheng et al. |
| 2010/0049334 A1 | 2/2010 | Okuda et al. |
| 2010/0094431 A1 | 4/2010 | Albrecht-Laatsch et al. |
| 2010/0228360 A1 | 9/2010 | Pusch et al. |
| 2010/0292807 A1 | 11/2010 | Velez et al. |
| 2011/0009981 A1 | 1/2011 | Okuda et al. |
| 2011/0270415 A1 | 11/2011 | Chen et al. |
| 2012/0330440 A1 | 12/2012 | Chen et al. |

FOREIGN PATENT DOCUMENTS

| | | |
|---|---|---|
| GB | 2 134 392 A | 8/1984 |
| JP | H03-30763 A | 2/1991 |
| SU | 1109153 A1 | 8/1984 |
| WO | 2008/072095 A2 | 6/2008 |

OTHER PUBLICATIONS

Product Brochure: New & Improved Total Knee by Ossur 2000/1900, 2010, 2 pages, www.ossur.com.

International Search Report and Written Opinion from International PCT Application No. PCT/US2012/040099 , dated Aug. 27, 2012.

International Search Report and Written Opinion from International PCT Application No. PCT/US2013/035432, dated Sep. 10, 2013.

Product Brochure: Rheo Knee, Walk Your Way, 2011, 20 pages, www.bionics.ossur.com.

Product Catalog: Uniprox Product Catalogue, 2010, Prosthetic Components, Orthoses and Materials. Ossur Americas, Foothill Ranch, CA, 2010, 8 pages, www.ossur.com, www.uniprox.de.

* cited by examiner

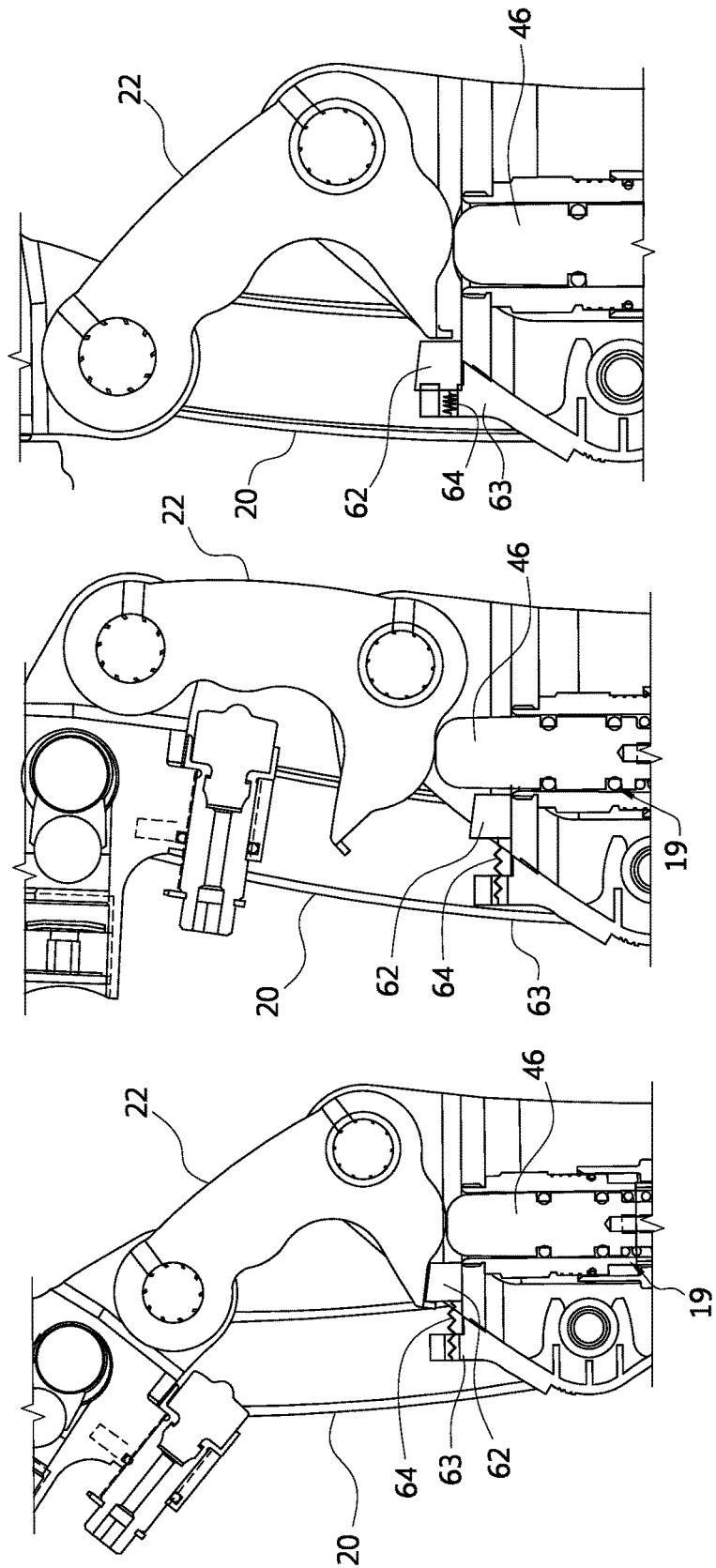

PROSTHETIC KNEE

FIELD OF THE INVENTION

The invention relates to a prosthetic knee in a prosthetic leg assembly, and more particularly to a prosthetic knee including a four bar geometry adapted for athletic uses.

BACKGROUND

Artificial limbs, including leg prostheses, employ a wide range of technologies to provide solutions suitable to many differing needs. For a trans-femoral amputee, basic needs in a leg prosthesis include stability, while standing and during the stance phase of a walking gait, and mechanical compatibility with the walking (or running) gait and some manner of knee flexion during stance and swing phases of a gait.

Certain trade-offs exist between security and stability, and walking or running performance (dynamic behavior). A simple, non-articulable leg (having no movable knee), may provide maximum stability, but does not provide for an ideal gait. Also, sitting may be awkward if a person cannot bend their knee.

There are no prosthetic knees tailored for high activity users, particularly athletes. For example, above-the-knee amputee sprinters and runners typically must resort to prosthetic knees designed primarily for walking purposes. From the selection of walking knees, the amputee engaged in athletic activities must compromise performance and durability of the knee.

SUMMARY

Under the embodiments of the invention, the prosthetic knee is designed to be used to deliver security and stability to amputees, particularly high activity amputees engaged in athletic activities, particularly sprinting or running.

The prosthetic knee is a multi-axial knee having stability adjustment to optimize the balance between knee stability and dynamic behavior for each individual user. The prosthetic knee allows for prevention of long term injury and discomfort, and facilitates improved gait characteristics to improve sprinting and running performance.

According to an embodiment, a prosthetic knee has a vertical axis, a locking head aligned to the vertical axis, a chassis extending obliquely relative to the vertical axis, and a plurality of links connecting the locking head to the chassis. The knee preferably has a four-bar geometry defined at least in part by the plurality of links for improved ground clearance.

The prosthetic knee has a swing control mechanism to control the flexion angle of a knee. The swing control mechanism includes a flexion stop connected to the chassis and extending outwardly from the chassis and obliquely relative to the vertical axis. The flexion stop may extend obliquely relative to the vertical axis at least by 90 degrees. The flexion stop is preferably a spring having a segment defining a generally flat surface.

The flexion stop is intended to stop the flexion of the knee by impacting on a prosthetic socket. The energy from the flexion (bending of the knee), the angular kinetic energy from a shank portion of the prosthesis is stored in the flexion stop, providing a powerful and fast extension of the shank portion, thus facilitating sprinting and running. The impact on the socket provides feedback to the user about the location of the prosthetic foot.

The prosthetic knee may include a bracket adjustably secured to the chassis and relative to the vertical axis, and the flexion stop is mounted to the bracket. The bracket defines at least one arcuate slot, and is adjustable relative to the chassis by the arcuate slot. The prosthetic knee may further include a fastener secured to the bracket at an angle relative to the chassis. The bracket is preferably adjustable to the vertical axis generally within the range of 0-30 degrees.

The chassis preferably defines a flat mounting surface extending obliquely relative to the vertical axis. The mounting surface extends relative to the vertical axis generally within the range of 10 to 35 degrees.

A mounting plate may be movably secured to the mounting surface by at least one fastener, without the necessity or inclusion of the bracket.

When starting a sprint in a competition, sprinters often use starting blocks where both knees are usually in a flexed position. Prosthetic knees used for sprinting are typically not load bearing in a flexed position, which means that so an amputee sprinter may get no forward propulsion from the prosthetic leg when pushing out of a starting block. To address this situation, the prosthetic knee may include a block lock. The block lock is manually activated to allow for load bearing in a flexed position which becomes inactive after one activation cycle of the runner (i.e., disengage when the knee is extended as the sprinter comes out of the starting block).

According to an embodiment of a block lock, the block lock has a spring loaded tab block preventing movement of a rear link when engaged therewith in flexion position. The tab block arranged to be pulled by the spring as the knee enters into extension and remain retracted to disengage from the rear link.

The prosthetic knee may include a housing and an eccentric friction brake including a friction shaft having an eccentric profile rotating in the housing as the knee rotates at an upper pivot point. A friction pad presses against the friction shaft, and is controlled by a spring element connected to the friction pad by a ball and a guide block. A friction screw allows for adjustment of preloading the spring element. As the friction shaft rotates, eccentricity of the friction shaft is arranged to change position relative to the other parts of the friction brake and compresses the spring element to increase a friction force on the friction shaft, and slow down rotation of the knee just before full extension is reached, without changing the rest of the swing phase of the knee.

To provide the user with information about the location of the rotation of the knee, an audio feedback mechanism is attached to a pivot axis of the prosthetic, and provides an audible sound as the knee rotates.

A prosthetic knee kit, includes a prosthetic knee having a vertical axis, and includes a locking head aligned to the vertical axis, a chassis extending obliquely relative to the vertical axis, a plurality of links connecting the locking head to the chassis. The kit has a plurality of flexion stops arranged to be connected to the chassis and extending outwardly from the chassis and obliquely relative to the vertical axis. Each of the flexion stops is arranged to be connected to the chassis at a plurality of different angles relative to the vertical axis.

The prosthetic knee may be equipped with an extension lock that provides stability and locking of the prosthetic knee in an extension position. Locking in an extension position may be beneficial in certain circumstances such as in running when there is an onset of runner fatigue in long distance running.

According to an embodiment of the extension lock, an arm is pivotally connected to the housing and arranged to engage a notch formed on at least one of the links. The extension lock may include first and second arms secured to one another by a handle bar. Tips of the first and second arms are configured to engage the first and second links, respectively. The notch may be formed on the links proximate to the housing.

When locking the prosthetic knee in an extension position, the handle bar is pushed upwardly so as to draw an arm segment into and make it engage notches formed by the links, which prevents further rotation of the links relative to the housing. The prosthetic knee may be unlocked by pulling the handle bar downwardly which draws the arm segment out from the notches. The extension lock may be retained in the disengaged configuration so as not to interfere with flexion and extension of the prosthetic knee, and is only selectively placed into the engaged, locked configuration when desired. The extension lock may be configured to operate in directions or movements different from those discussed above, such as by a reversal of directional movement. A spring may bias the handle bar so that it is maintained in the disengaged configuration.

The numerous other advantages, features and functions of embodiments of a prosthetic knee are readily apparent and better understood in view of the following description and accompanying drawings. The following description is not intended to limit the scope of the prosthetic knee, but instead merely provides exemplary embodiments for ease of understanding.

BRIEF DESCRIPTION OF THE DRAWINGS

These and other features, aspects, and advantages of the present invention will become better understood regarding the following description, appended claims, and accompanying drawings where:

FIG. 11 is a sectional view of the prosthetic knee in a prosthetic leg assembly in a flexion configuration wherein a variation of a brake is in a blocked position.

FIG. 12 is a sectional view of the prosthetic knee in a prosthetic leg assembly in an extension configuration wherein the brake of FIG. 11 is in an unblocked position.

FIG. 13 is a sectional view of the prosthetic knee in a prosthetic leg assembly in a flexion configuration wherein the brake of FIG. 11 is in an unblocked position.

Figure 1:
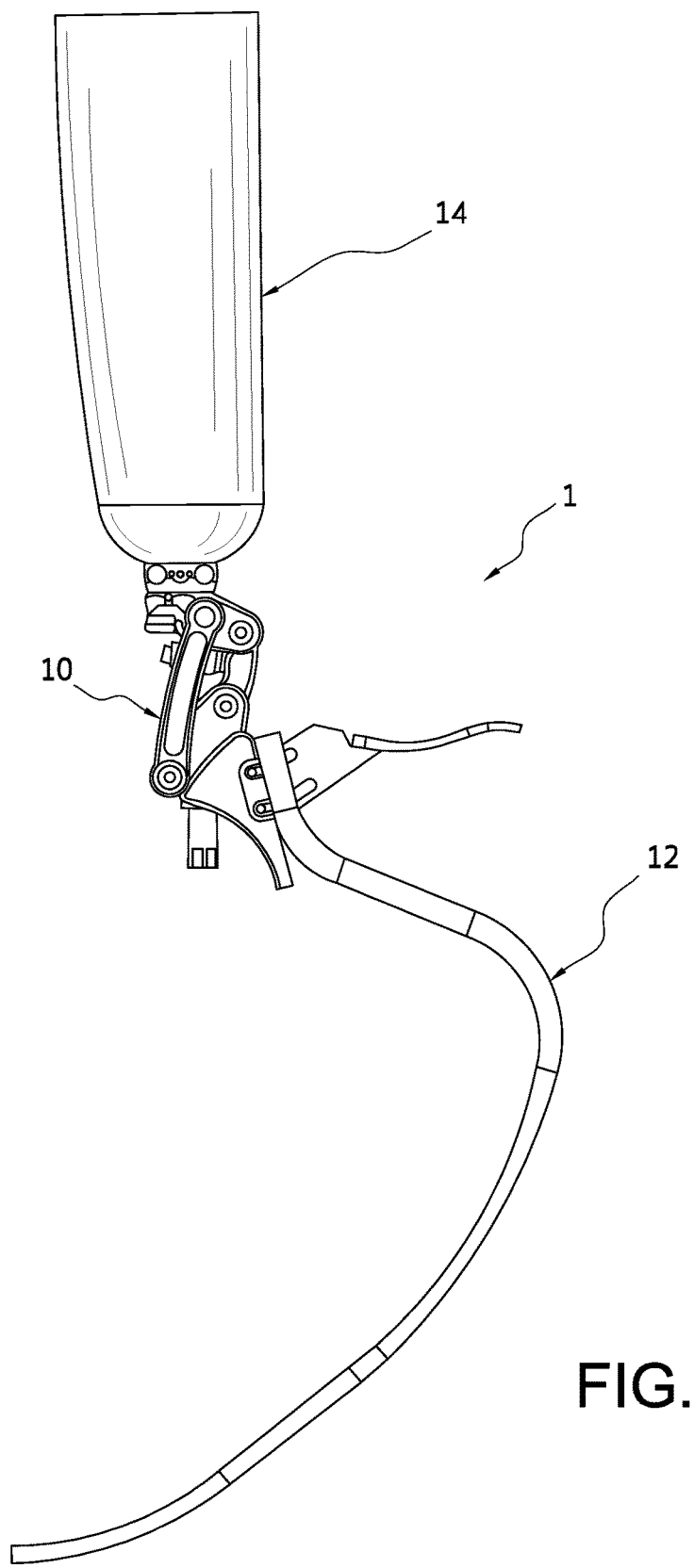
FIG. 1 is an assembly view showing a prosthetic leg assembly including a prosthetic knee.

The drawing figures are not necessarily drawn to scale, but instead are drawn to provide a better understanding of the components, and are not intended to be limiting in scope, but rather to provide exemplary illustrations. The figures illustrate exemplary embodiments of a prosthetic knee and the components, and in no way limit the structures or configurations of a prosthetic knee and components according to the present disclosure.

DETAILED DESCRIPTION OF VARIOUS EMBODIMENTS

A. Environment and Context

To understand the operation of the prosthetic knee described, a basic discussion of the gait cycle is required. A gait cycle defines the movement of the leg between successive heel contacts of the same foot. The gait cycle has two phases: stance and swing. The stance phase has three time periods: heel-strike, mid-stance and toe-off.

During mid-stance, the knee joint will be at full extension. An actual knee joint will have some flexion between heel-strike and mid-stance and between mid-stance and toe-off. This is called "stance flexion." Not all prosthetic joints provide for stance flexion, and for those that do, they are mechanically complex, expensive, or both. These prosthetic joints typically require frequent maintenance and replacement. The amount of stance flexion required can vary from user to user, while most prosthetic joints have no adjustability.

Maximum flexion of the knee joint, while walking, will occur at the end of the toe-off phase. The maximum flexion is typically determined in part by the speed at which a person is walking. The faster a person walks, the greater the maximum flexion, while the slower a person walks, the lesser the maximum flexion. In a natural knee, the maximum flexion can be controlled and limited via the musculature of the leg. In a prosthetic knee joint, some artificial means of controlling and limiting the maximum flexion is typically provided. Immediately following the end of the toe-off phase begins the swing phase.

While the stance phase has three time periods, the swing phase has two time periods: acceleration and deceleration. The acceleration phase begins immediately following the maximum flexion during the toe-off phase. During the acceleration phase, the lower portion of the leg, comprising the shin and foot, swings back towards full extension. In a natural knee joint, a deceleration phase follows the acceleration phase, during which the lower portion of the leg continues to swing towards full extension. Some prosthetic joints do not provide for any deceleration during the swing phase. Other prosthetic joints provide deceleration by using costly and bulky hydraulic or pneumatic cylinders. The deceleration required can vary from user to user, while most prosthetic joints have no adjustability.

For further ease of understanding the joint disclosed, a description of a few terms is necessary. As used, the term "upper" has its ordinary meaning and refers to a location above, or higher than another location. Likewise, the term "lower" has its ordinary meaning and refers to a location below, or underneath another location. The term "rear" is used interchangeably with the term "posterior," and also has its ordinary meaning and refers to a location that is behind or to the rear of another location. The term "front" is used interchangeably with the term "anterior," and has its ordinary meaning and refers to a location that is ahead or to the front of another location.

B. Exemplary Embodiments

FIG. 1 illustrates the general configuration of a prosthetic leg assembly 1 for an above-the-knee or transfemoral amputee. The leg assembly 1 includes a prosthetic knee 10, a socket 14 connected to the knee 10 and arranged to receive the residual limb, and a prosthetic foot 12.

The emphasis of this disclosure is on the prosthetic knee. The socket may be constructed and configured under any known methods and structures described in at least U.S. Pat. No. 7,438,843, granted Oct. 21, 2008, and incorporated by reference. An exemplary foot, such as the one depicted in FIG. 1, may be the CHEETAH foot sold by Ossur hf of Reykjavik, Iceland, and a "running foot."

Figure 2:
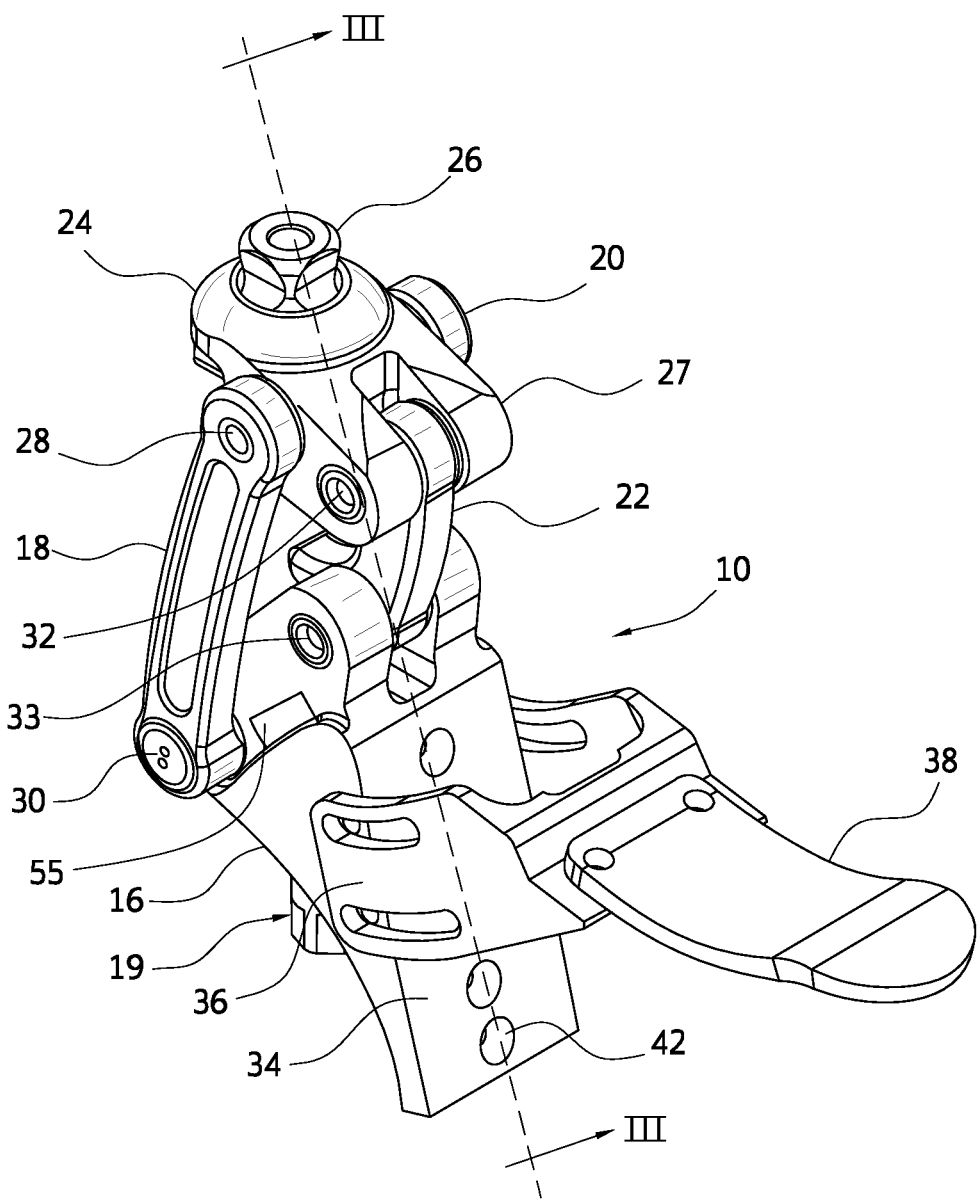
FIG. 2 is a perspective view of an embodiment of a prosthetic knee.
Figure 3:
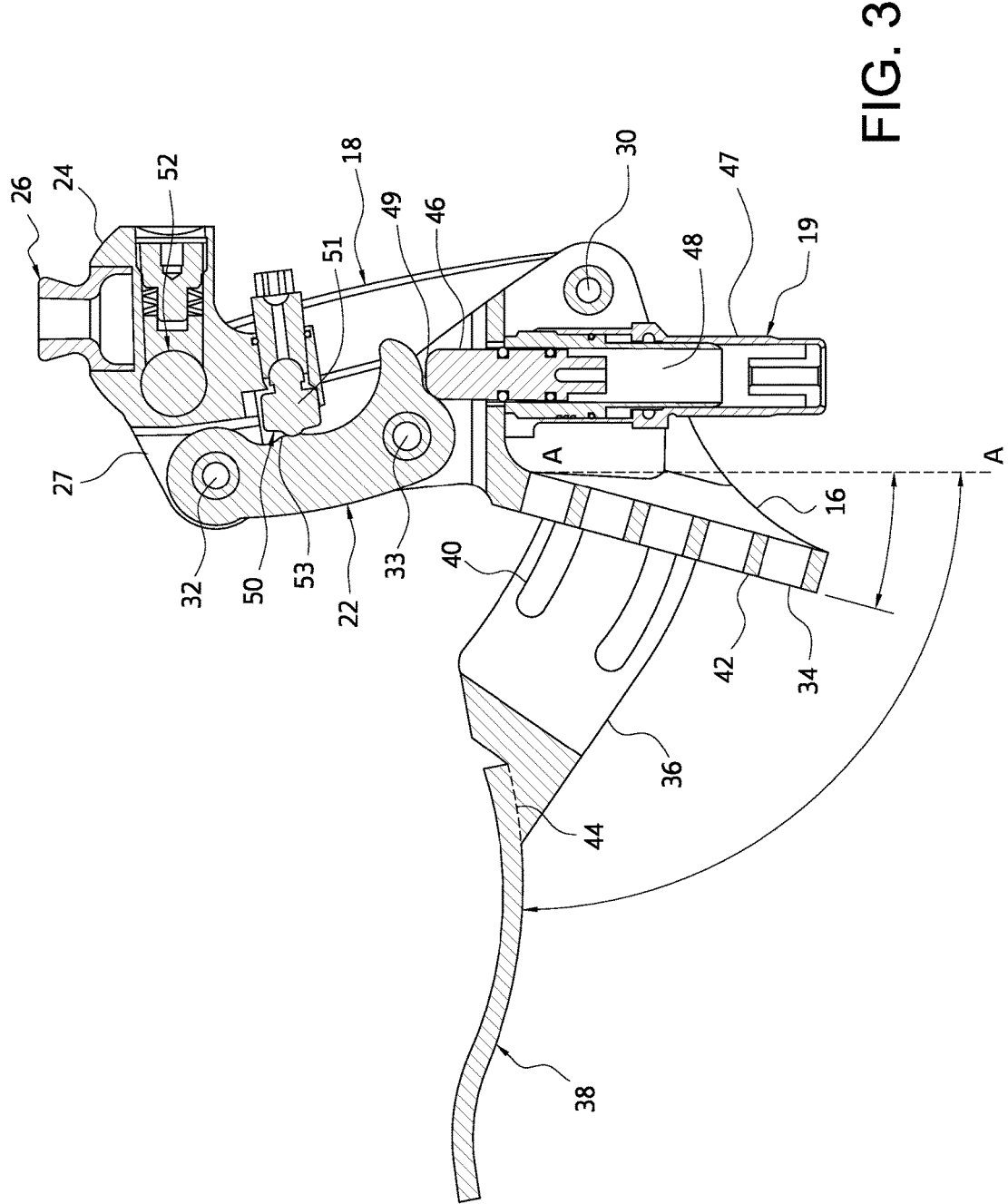
FIG. 3 is a cross-sectional elevational view of the prosthetic knee taken along line III-III in FIG. 2.

An exemplary embodiment of a prosthetic knee 10 is shown in FIGS. 2 and 3. As shown, the prosthetic knee includes a housing 24, parallel front links 18, 20, a rear link 22, and a chassis 16. The prosthetic knee 10 includes a locking head 26, in the preferable form of a pyramid adapter, at the top and a distal mounting surface 34. The front links and the rear link may be constructed under the prosthetic knee described in co-pending U.S. provisional application No. 61/491,707, filed on May 31, 2011.

The front links 18, 20 are oriented, sized and located to provide for stability. The front links 18, 20 are on and pivotally connected to opposed sides of the chassis 16 and the housing 24, and pivot at upper and lower pivot points 28, 30. The rear link 22 pivotally connects to a housing flange 27 extending posteriorly from the housing 24 and to the chassis 16, and pivots at upper and lower pivot points 32, 33.

Of particular note, the front links 18, 20 both extend above the rear link 22 and substantially below the rear link 22. However, the front links 18, 20 are not too long for this leads to poor torsion whereas the front links 18, 20 are not too short for this makes it difficult to fit the prosthetic knee 10.

Besides the selection of the length of the links as parameters for designing the knee, both the flexion factor (i.e., large angle of locking and easy swing initiation) and a large flexion angle which allows for adapter clearance at 130 and 140 degrees are considered. Additional parameters include locating the links for the greatest toe clearance, good stability, ease of swing initiation, and good maximum flexion for both the clamp attachment and pyramid adapter.

The mounting surface 34 is arranged for securing directly to the running foot configured for running which often connect to a knee via a pylon and ankle apparatus. The mounting surface 34 is preferably flat, and is arranged at an oblique angle relative to a vertical axis A-A. The angle of the mounting surface relative to a vertical axis may be 15 to 25 degrees. The running foot may be secured to the mounting surface 34 by a plurality of fasteners (not shown) received in openings 42 located along the mounting surface 34.

A flexion stop 38 is mounted on a bracket 36 that is adjustably secured to the chassis 16. The flexion stop 38 is arranged to stop the flexion of the knee by impacting the socket. Angular kinetic energy from the flexion or bending of the knee is stored in the flexion stop, urging the knee into a powerful and fast extension to facilitate sprinting or running. The impact of the flexion stop on the prosthetic socket provides feedback to the user about the location of the prosthetic foot.

According to this variation, the bracket 36 is adjustably arranged relative to the chassis 16, and hence the flexion stop 38, with at least one arcuate slot 40 on opposed sides of the bracket 36. The angle of the flexion stop 38 relative to a vertical axis A-A can be adjusted accordingly by tightening the bracket 36 along the at least one slot 40 to the chassis 16 by suitable fasteners. A preferable range of adjustment corresponding to the slots is about 0-25 degrees from the vertical axis. The flexion stop 38 can be secured to the bracket 36 along a generally flat surface 44.

According to this embodiment, the flexion stop is constructed from a carbon fiber spring, although other materials may be employed such as polymers and composites. To prevent damage of the flexion stop or the prosthetic socket, a pad of cushioning material may be adhered to the end of the flexion stop or the prosthetic socket. As depicted in FIG. 3, the flexion stop may be elongate and define a compound curve, although other configurations are possible such as straight or curved, or a combination of the same.

Figure 4:
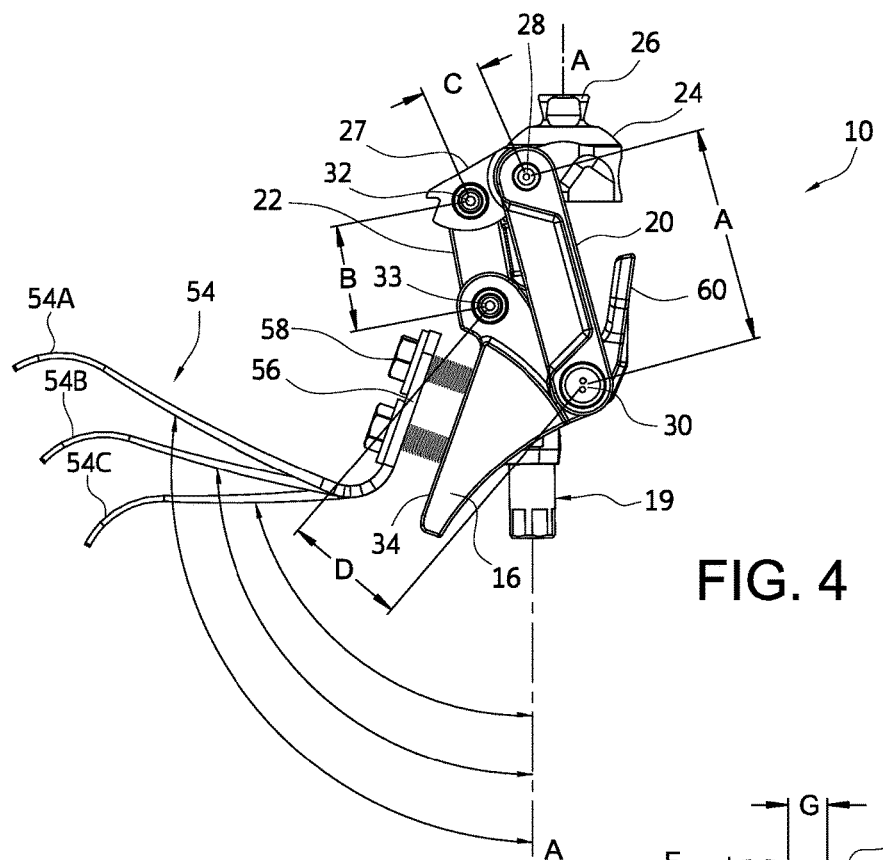
FIG. 4 is an elevational view of another embodiment of a prosthetic knee showing dimensions of various components.
Figure 5:
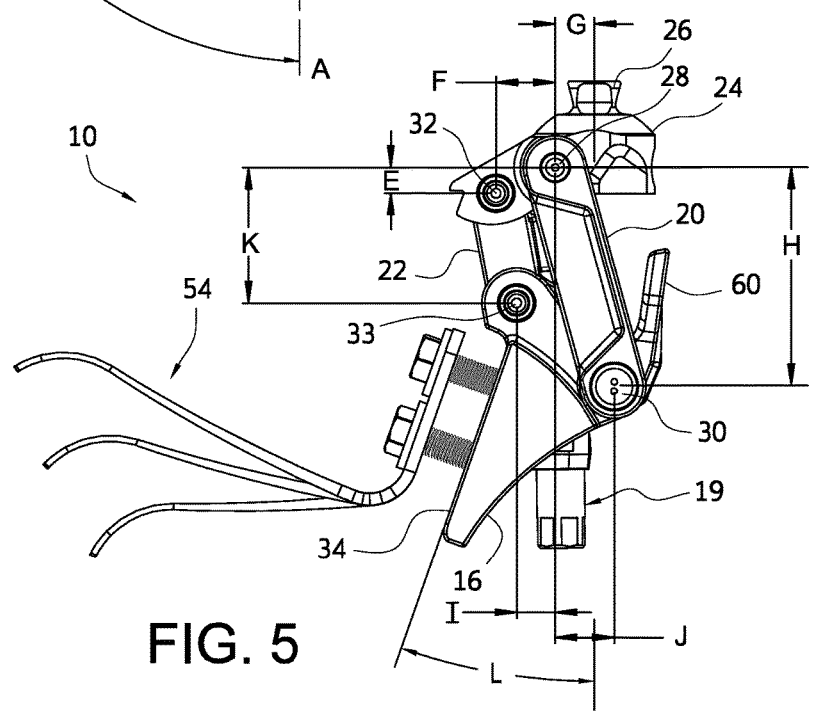
FIG. 5 is the elevational view of FIG. 4 and shows spatial relationships among the components.

In reference to FIGS. 4 and 5, an embodiment of the prosthetic knee is shown having a different flexion stop and means for attachment. FIG. 4 illustrates a flexion stop 54 having a plurality of predetermined configurations 54A-54C which permit the user to select which of the configurations 54A-54C to use. The configurations 54A-54C are arranged at different angles relative to the vertical axis A-A. The flexion stops 54A-54C are arranged incrementally at angles 100-120 degrees respectively relative to the vertical axis A-A.

Unlike in the embodiment of FIGS. 2-3, the attachment variation in FIG. 4 does not include variable adjustment, in part in view of the selection of different flexion stops, and includes a plate 56 secured to the mounting surface 34 by a plurality of fasteners 58.

Regarding the spatial relationship among the components of the prosthetic knee, FIGS. 4 and 5 show the ranges of various ratios of locations among the pivot points 28, 30, and 32, 33 and the lengths of the links relative to one another, taking 1.0 as the base number. Particularly, the relative locations of the links and their positions relative to attachments in the form of the pyramid adapter and the clamp attachment determine their geometry and spatial relationships.

| Dimension | Ratio |
| --- | --- |
| A | 7.3-7.7 |
| B | 3.5-3.9 |
| C | 2.0-2.2 |
| D | 4.0-4.4 |
| E | 0.8-0.9 |

-continued

| Dimension | Ratio |
| --- | --- |
| F | 1.85-2.05 |
| G | 1.2-1.4 |
| H | 7.0-7.4 |
| I | 1.2-1.35 |
| J | 1.85-2.05 |

Because the prosthetic knee is arranged for sprinting or running, the linkage lengths and locations of the pivots are selected considering there is no heel strike, since at least the running foot does not have a heel, as compared with conventional prosthetic feet. In conventional feet, the linkage lengths and the pivot points are selected for stability at heel strike while maintaining a relatively easy release at flexion at late stance or toe off. In a prosthetic knee arranged for sprinting or running, stability is of less concern since many athletes have powerful hips which enable them to actively stabilize the knee joint as required.

Certain parameters to consider include ground clearance with mid swing shortening due to the geometry of the prosthetic assembly. Another parameter includes a large range-of-motion in the knee since many runners flex their knee up to 150 degrees. A low overall height is of concern for the knee since running feet are long, and should fit on short amputees. Parallel vertical linkages should be avoided or minimized since if the front links and the rear link reach a position where they are parallel, the instantaneous center of rotation shifts from being far above the knee to being far below the knee. This can cause an undesirable significant jolt or impact on the residual limb (referred as "terminal impact") at high running speeds.

1. Swing Control Mechanisms

The prosthetic knee has a variety of swing control mechanisms that allow for control of both extension and flexion of the prosthetic knee.

The flexion stop 38 is provided to control the flexion angle of the prosthetic knee, and operates by controlling flexion by adjustment of the angle the flexion stop is mounted to the chassis. The flexion stop also provides extension assist by having stored energy upon impact by the prosthetic socket, which urges the knee away from the prosthetic socket into extension.

In reference to FIG. 3, the prosthetic knee also includes an extension assist mechanism 19. The extension assist mechanism includes the extension assist piston 46, which is retained in an inner housing 48, which remains fixed, with an extension assist spring. Seals, such as O-rings, are provided between the external surface of the extension assist piston 46 and the internal surface of the inner housing 48.

The upper end of the inner housing 48 is held in a first hole in the chassis 16 between the upwardly extending flanges, so the extension assist piston 46 can be biased into engagement with the lower end 49 of the rear link 22, as discussed below.

An adjustable external housing 47 is positioned within the chassis 16, and is provided coaxially with the inner housing 48, and receiving the inner housing 48 (and the extension assist piston 46) with the seal located therebetween, and a spring guide and the extension assist spring. The spring guide engages a bottom end of the extension assist spring, and the upper end of the extension assist spring engages a bottom end of the extension assist piston 46.

By accessing the adjustable external housing 47, a clinician can rotate the adjustable external housing 47 in a vertical direction (upwards or downwards) to alter the compression of the extension assist spring, and alter the biasing force applied to the extension assist piston 46 by the extension assist spring, and therefore the biasing force applied to the rear link 22 by the extension assist piston 46. In this manner, the extension assist mechanism allows for adjustment to the individual user's speed, by adjusting the outer housing.

As also shown in FIG. 3 and described in U.S. provisional application No. 61/491,707, the prosthetic knee also includes an extension stop 50 which further limits extension of the knee. The extension stop 50 includes a stability adjustment screw connected to a bumper 51 which is struck a raised surface 53 on the rear link 22. The extension stop 50 balances between stability and dynamic behavior of the prosthetic knee. It allows the clinician to match the prosthetic knee to the needs and behavior of the wearer by tightening or loosening the stability adjustment screw, which alters the position of the bumper.

The extension stop prevents further extension of the knee. When the knee reaches full extension, the user can feel the terminal impact through the prosthetic socket. While the terminal impact provides the user tangible feedback, it should be dampened to prevent long term injury or discomfort to the user, and facilitate improved gait characteristics to improve sprinting or running.

Besides the aforementioned extension stop, other devices may be used alone or in combination with one another to handle terminal impact. The prosthetic knee may be provided with a hydraulic damper, a double durometer bumper besides the bumper 51 which may be on the rear link, a constant friction brake mechanism as described in U.S. provisional application No. 61/491,707, or an eccentric friction brake.

Figure 6:
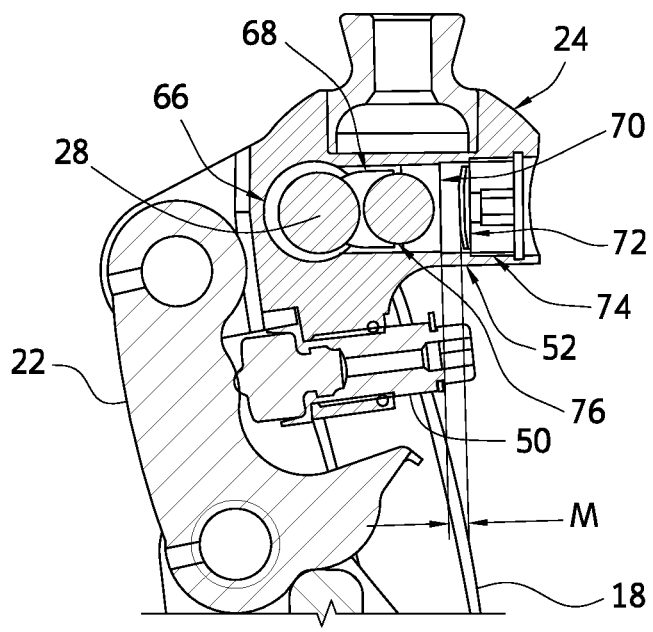
FIG. 6 is a cross-sectional elevational view showing an extension stop in a first position.
Figure 7:
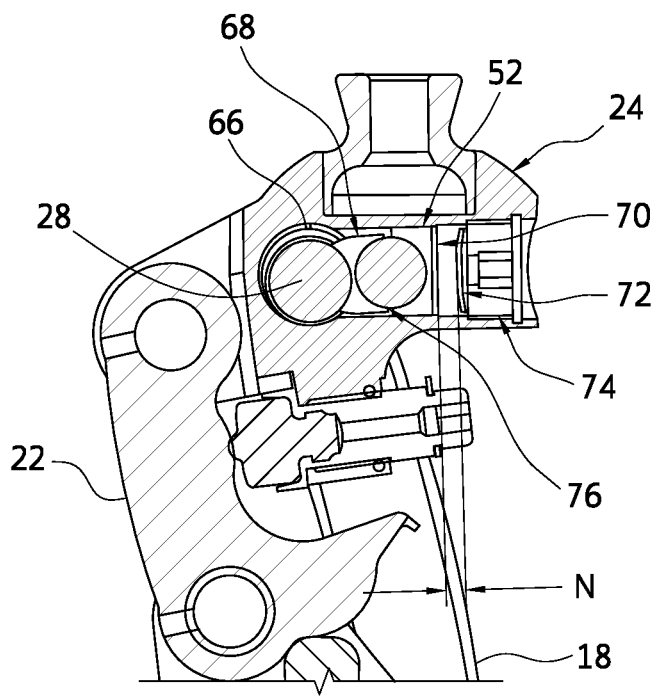
FIG. 7 is a cross-sectional elevational view showing the extension stop of FIG. 6 in a second position.

FIGS. 6-7 depict an embodiment of an eccentric friction brake 52. A friction shaft 66 having an eccentric profile rotates in the housing 24 as the knee rotates at the upper pivot point 28. A friction pad 68 presses against the friction shaft 66, and is controlled by a spring element 72, such as at least one disc spring, which is connected to the friction pad 68 by a ball 76 and a guide block 70. A friction screw 74 allows for adjustment of preloading the spring element 72.

In operation, as the friction shaft 66 rotates, the eccentricity of the shaft changes position relative to the other parts of the friction brake and compresses the spring element 72, as evidenced by the different dimensions M and N between the friction screw 74 and the guide block 70 in FIGS. 6 and 7. This results in an increase in force exerted on the friction pad 68, and increases the friction force on the friction shaft 66, slowing down the rotation of the knee just before full extension is reached, without changing the rest of the swing phase of the knee.

In a variation of the friction brake, a hydraulic fluid may replace the spring element, and provides increased ability to control the extension of the knee separately.

2. Block Mechanism

When a sprinter starts in a competition, a starting block is typically used. When in position with the starting blocks, both knees are in a flexed position. Since prosthetic knees used for sprinting are not configured for load-bearing in a flexed position, an amputee sprinter has no forward propulsion from the prosthetic leg when initially pushing from the starting block. The block mechanism must become inactive after the initial push off from the starting blocks and remain disengaged from the housing so as not to interfere with further use of the knee during the sprint.

In FIGS. 8-13, two block mechanisms are shown for providing the initial assist only required at the initial push off from the starting blocks.

Figure 10:
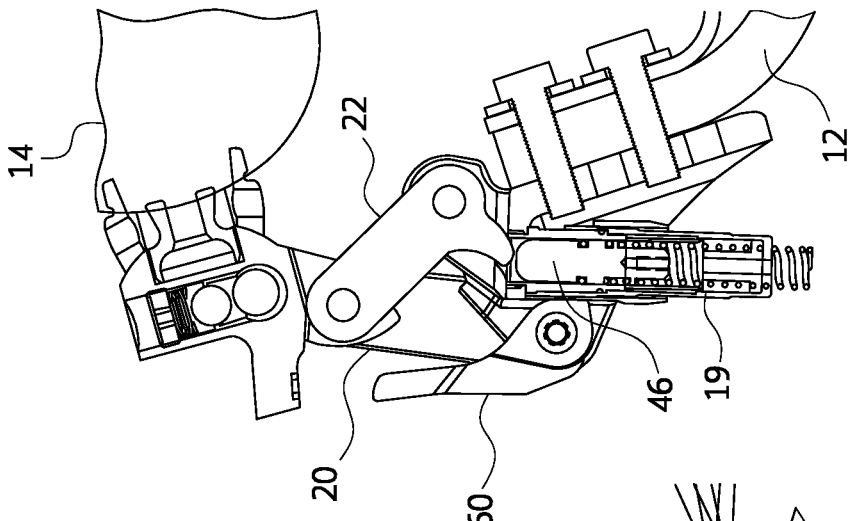
FIG. 10 is a sectional view of the prosthetic knee of FIG. 5 in a prosthetic leg assembly in a flexion configuration wherein the brake is in an unblocked position.
Figure 9:
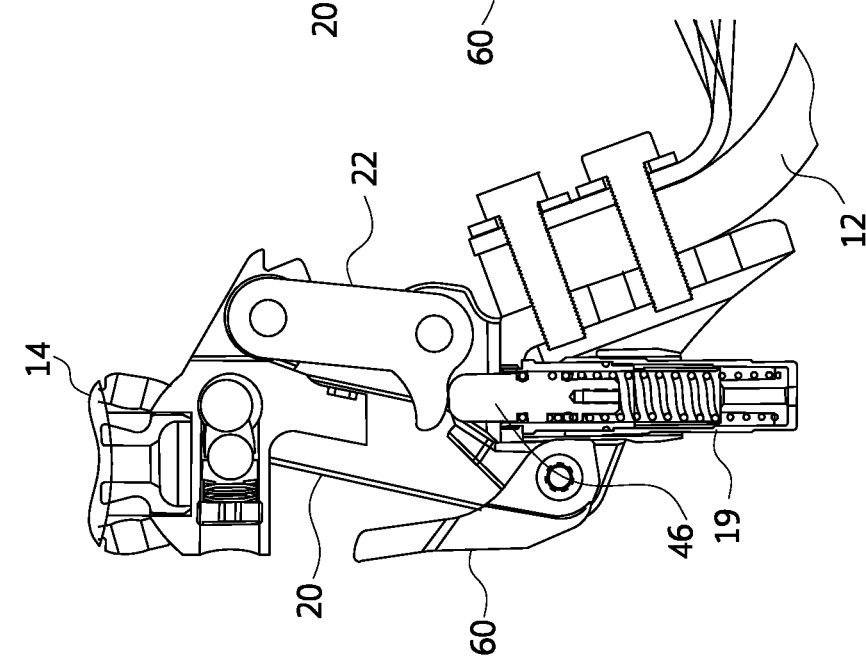
FIG. 9 is a sectional view of the prosthetic knee of FIG. 5 in a prosthetic leg assembly in an extension configuration wherein the brake is in an unblocked position.
Figure 8:
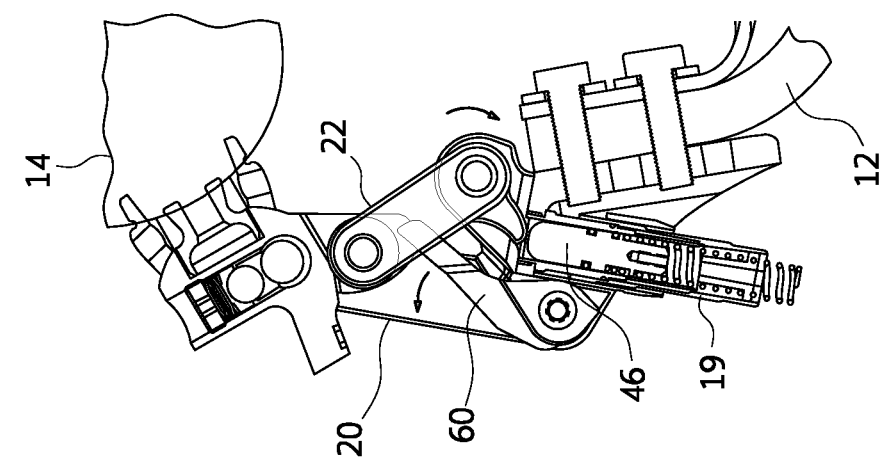
FIG. 8 is a sectional view of the prosthetic knee of FIG. 5 in a prosthetic leg assembly in a flexion configuration wherein the brake is in a blocked position.

In observing FIGS. 8-10, a block mechanism in the form of a pivotable blade block 60 is manually arranged to block movement of the housing relative to the chassis, and maintain the knee in a flexed position, as shown in FIG. 8. Upon initial push off from the starting blocks, the blade block 60 is released from locking the housing relative to the chassis, as shown in FIG. 9 wherein the leg is in extension. A spring (not shown) may assist placing the blade lock away from the housing and chassis. FIG. 10 shows the knee as it is in flexion subsequent to the initial push off wherein the blade lock 60 is maintained from engaging the housing.

In another embodiment of the block mechanism, FIG. 11 depicts a tab block 62 which prevents movement of the rear link 22 when engaged therewith. When the knee extends, as shown in FIG. 12, a spring 64 pulls the tab block 62 toward a front side 63 of the chassis. When the knee goes back into flexion, as illustrated in FIG. 13, the tab block 62 remains completely disengaged from the rear link 22.

3. Audible Feedback Mechanism

Figure 14:
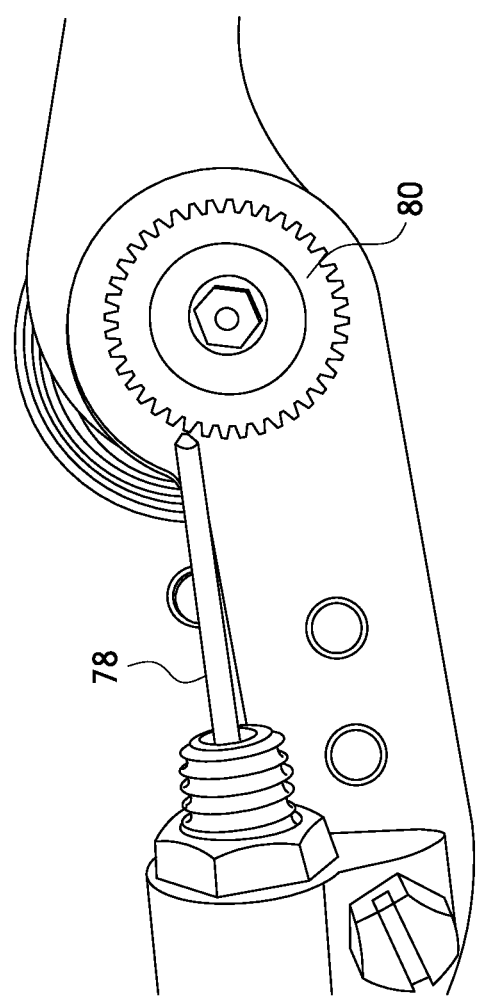
FIG. 14 is an embodiment of an audio feedback mechanism.

An audio feedback mechanism may provide the user with information about the location of the rotations of the prosthesis. As illustrated in FIG. 14, an audible feedback embodiment includes a gear wheel 78 attached to one of the pivot axes of the knee. A spring loaded pin 80 is fixed to another structural part of the knee and engages the gear wheel 78 as the gear wheel 78 rotates in relation to the pin 80. During this rotation, an audible sound is produced.

The audible sound changes in frequency with the speed of the knee and a notable change in pitch is observed as the knee changes in rotational direction. This allows the user to get a better feeling for the location and/or speed of the shank in space improving performance and safety. Other mechanisms may also be used for providing position, velocity or acceleration related feedback to the user.

4. Swing Control Adjustability

Figure 17:
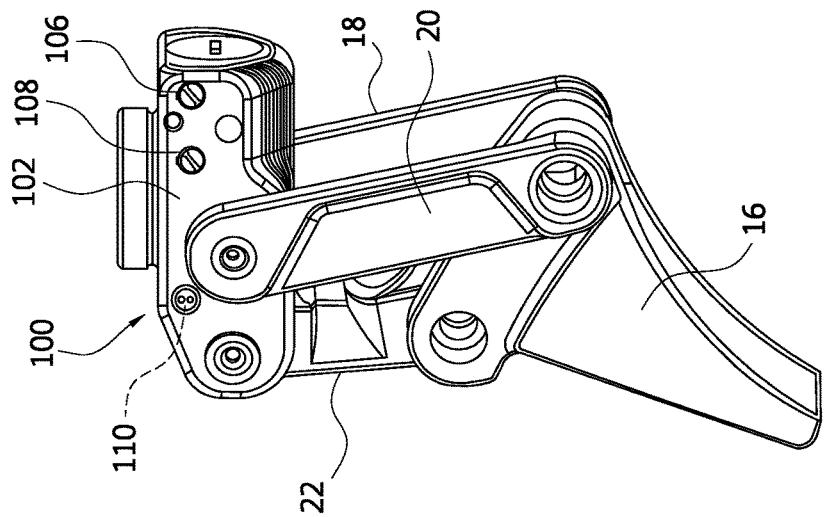
FIG. 17 is a perspective view of the prosthetic knee embodiment of FIG. 15.
Figure 16:
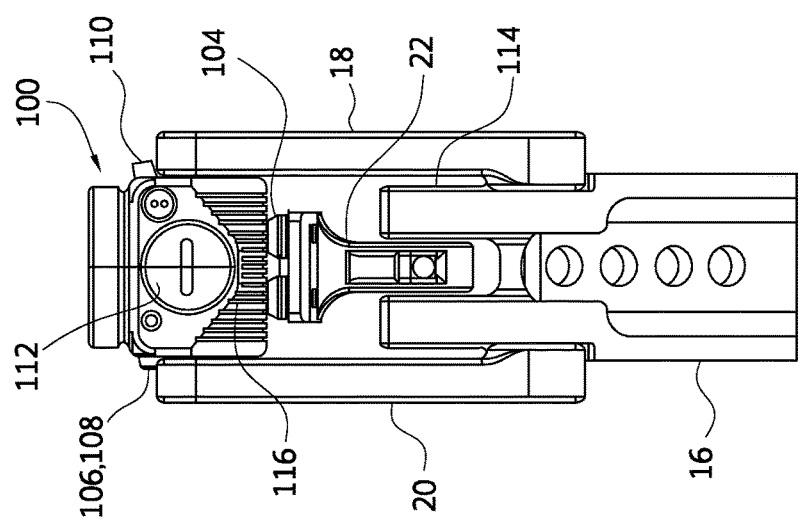
FIG. 16 is an elevational frontal view of the prosthetic knee embodiment of FIG. 15.
Figure 15:
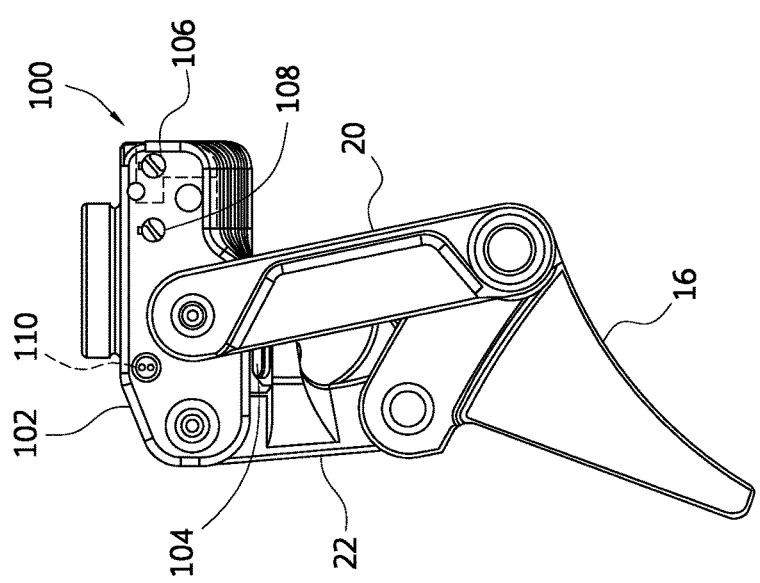
FIG. 15 is an elevational side view of a prosthetic knee embodiment having swing control adjustability.

The prosthetic knee embodiment 100 according to FIGS. 15-17 has swing control adjustability in the housing 102. As with the embodiment of FIG. 2, the prosthetic knee 100 includes a chassis 16, front links 18, 20, and a rear link 22.

The swing control adjustability features of the prosthetic knee 100 are similar to the swing control adjustability features provided in the prosthetic knee products offered by Ossur hf of Reykjavik, Iceland, and having product names TOTAL KNEE 1900, TOTAL KNEE 2000 and TOTAL KNEE 2100. Although the prosthetic knee embodiment includes swing control adjustability features, they are configured for running or elevated uses above normal walking, and are in combination with other features of the prosthetic knee embodiments discussed.

According to the prosthetic knee 100, the rear link 22 has bumpers 104 adapted to strike an undersurface of the housing 102. The bumpers 104 minimize any shock incurred during extension of the prosthetic knee, and protect the housing 102 from damage.

Regarding swing control adjustability, the housing 102 defines hydraulic resistance adjustability by way of a plurality of valves 106, 108, 110. The first valve 106 is arranged to control flexion resistance from 60 degrees to a full or complete flexion position. The second valve 108 is arranged to control resistance from full extension to 60 degrees (0-60). The third valve 110 may be on an opposite side of the first and second valves 106, 108. The third valve 110 controls extension resistance. If the third valve 110 is turned clockwise, the valve is closed which increases resistance; if the third valve 110 is turned counterclockwise, the valve is opened which decreases resistance.

A friction adjustment valve and screw 112 may also be used in combination with the other swing control adjustability features. The friction adjustment valve and screw 112 allows for adjustment to increase or decrease friction with an elastic polymer medium, so the swing phase of the prosthetic knee 100 is controlled and steady.

The prosthetic knee 100 may also include an extension promoter 114 provided to reduce excessive heel rise. Clockwise rotation decreases heel rise, whereas counterclockwise rotation increases heel rise (when already having been decreased).

Each of these swing control adjustability features is arranged in a manner to withstand the rigors of active amputees, including intense athletic activities. The valves are provided with increased fluid capacity over known models to better resist flexion and control swing. The valves may likewise be relocated over known prosthetic knees to accommodate the larger valves and increased fluid capacity. The prosthetic knee 100 may include fins 116 to cool the knee due to the resistance which occurs by the increased valve size.

5. Extension Lock

FIGS. 18-21 show a prosthetic knee embodiment 118 sharing certain features with the prosthetic knee 100, and including upper and lower pyramid adapters 26, 120 and an extension lock 124. In this embodiment, the foot connection has the lower pyramid adapter 120 which replaces the direct connection shown in the embodiments associated with FIG. 13. The flexion stop 54 may be directly connected to an inclined surface 122 of the rear link 22.

The extension lock 124 pivotally connects to the housing 102 and engages notches 132 formed on the front links 18, 20. The extension lock 124 includes a first arm segment 126 pivotally attached to the housing 102 by a fastener 128 which permits a second arm segment 130 to engage or disengage with the notch 132. Each side or arm of the extension lock 124 corresponds to the front links 18, 20, respectively, and these sides are connected by an elongate handle bar 134 located on the front of the prosthetic knee. A tip 136 of the second arm segment has a complementary shape to the notch 132 so as to assure engagement and retention with the notch 132.

Figure 18:
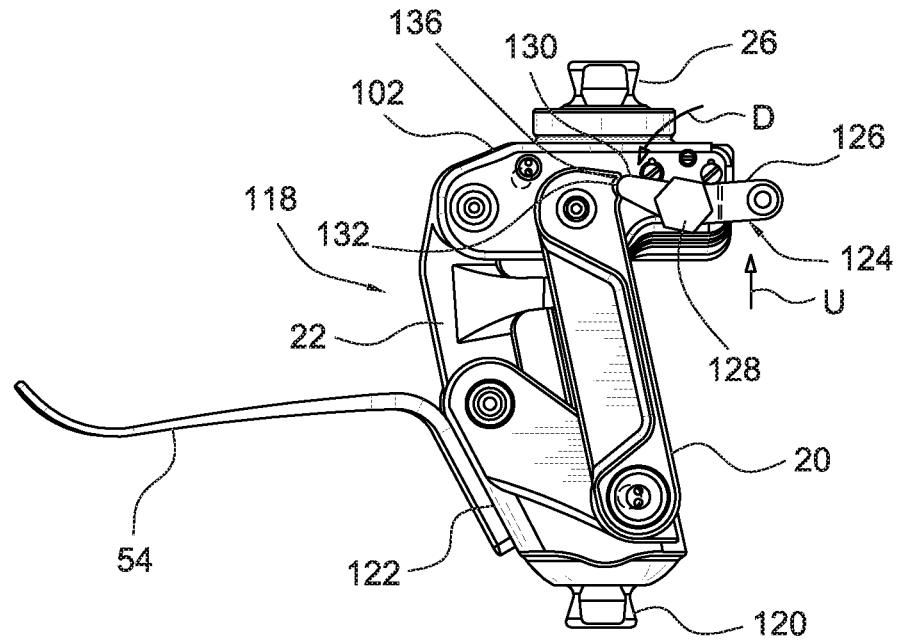
FIG. 18 is an elevational side view of a prosthetic knee embodiment having an extension lock in an engaged position.
Figure 19:
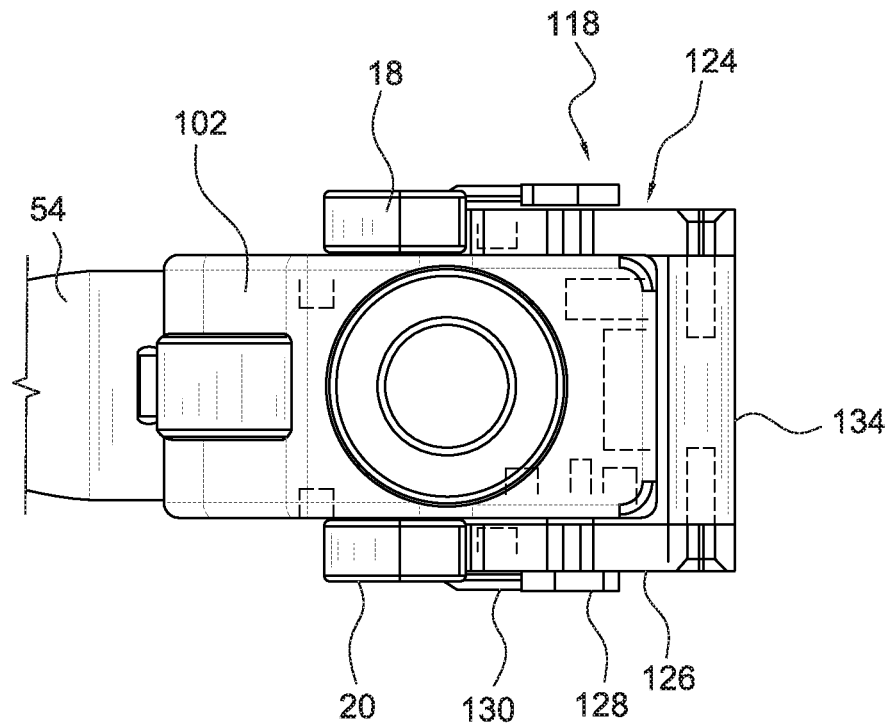
FIG. 19 is a sectional plan view of the prosthetic knee embodiment of FIG. 18.

FIG. 18 shows the prosthetic knee 118 in an extension configuration with the extension lock 124 engaging the front links 18, 20. This may be accomplished by pulling the handle bar 134 upwards U which in turn draws the second arm segment 130 downwards to engage the notch 132. Once engaged, the second arm segment rests within the notch, thereby preventing rotation and maintaining the prosthetic knee in extension.

Figure 20:
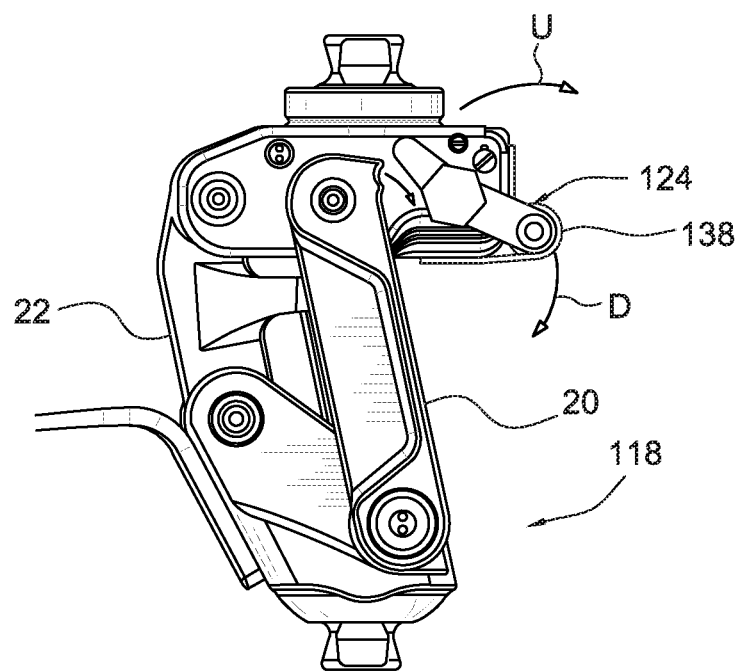
FIG. 20 is a sectional side view of the prosthetic knee embodiment of FIG. 18 in extension with the extension lock in a disengaged position.
Figure 21:
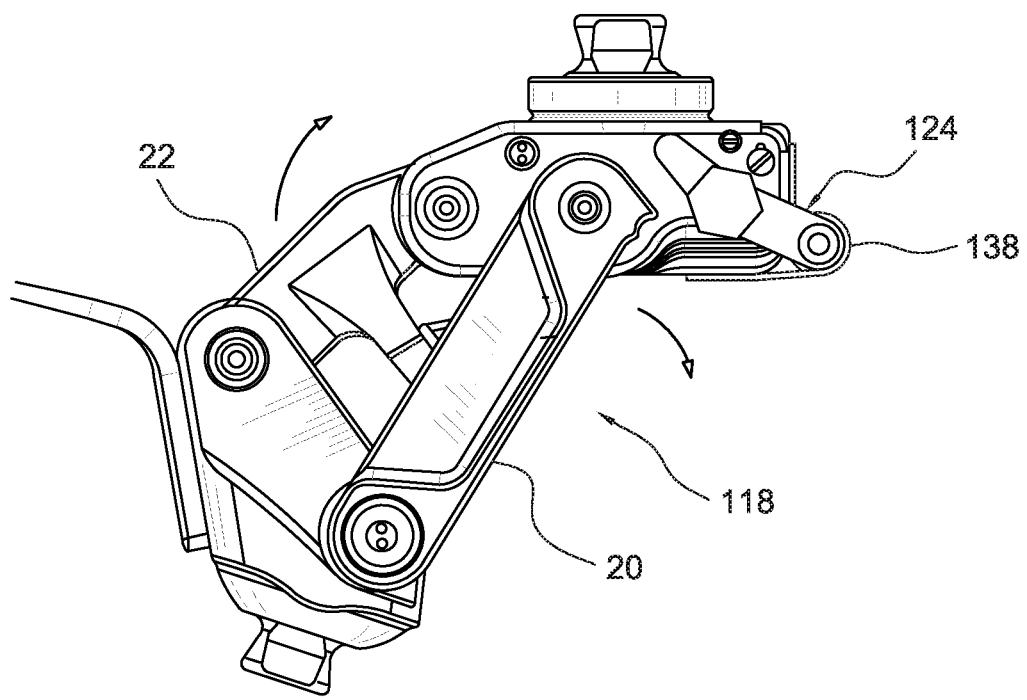
FIG. 21 is a sectional side view of the prosthetic knee embodiment of FIG. 18 in flexion with the extension lock in a disengaged position.

FIG. 20 illustrates the prosthetic knee 118 with the extension lock 124 disengaged from the front links 18, 20, thereby permitting rotation or flexion of the prosthetic knee. This is accomplished by pulling downwardly on the handle bar which draws the second arm segment out from the notch. FIG. 21 depicts the prosthetic knee 118 in flexion with the extension lock 124 fully disengaged. When disengaged, the prosthetic knee can rotate back and forth from flexion and extension without interference from the extension lock 124.

A spring arrangement 138 is arranged to bias the extension lock 124 in the disengaged position so as to avoid interference with movement of the links. The handle bar 134 may be pushed upwardly against resistance from the spring to place the tip 136 in the notch 132, and allow the tip 136 to maintain engagement with the notch 132 when the prosthetic knee is in the extension configuration.

FIGS. 20 and 21 depict a torsion spring 138 that wraps about or engages the handle bar and biases against the housing 102. Alternative spring arrangements may be employed such as a clip configuration engaging at least part of the handle bar and biasing against the housing, or a flat, leaf biasing against the handle bar and the housing. The springs may be constructed from a variety of materials, and the handle bar and/or housing may be adapted with notches or grooves to retain the spring.

Not necessarily all such objects or advantages may be achieved under any embodiment of the invention. For example, those skilled in the art will recognize that the invention may be embodied or carried out to achieve or optimize one advantage or group of advantages as taught without achieving other objects or advantages as taught or suggested.

The skilled artisan will recognize the interchangeability of various components from different embodiments described. Besides the variations described, other known equivalents for each feature can be mixed and matched by one of ordinary skill in this art to construct an orthopedic device under principles of the present invention. Therefore, the embodiments described may be adapted to orthopedic systems for securing, supporting or comforting limbs or other anatomy.

Although this invention has been disclosed in certain preferred embodiments and examples, it therefore will be understood by those skilled in the art that the present invention extends beyond the disclosed embodiments to other alternative embodiments and/or uses of the invention and obvious modifications and equivalents. It is intended that the scope of the present invention disclosed should not be limited by the disclosed embodiments described above, but should be determined only by a fair reading of the claims that follow.

The invention claimed is:

1. A prosthetic knee, comprising:
   a housing;
   a chassis;
   a plurality of links pivotally connecting the housing to the chassis;
   an eccentric friction brake including a friction shaft having an eccentric profile rotating in the housing as the knee rotates at an upper pivot point; and
   a friction pad presses against the friction shaft, and controlled by a spring element connected to the friction pad.

2. The prosthetic knee of claim 1, wherein as the friction shaft rotates, eccentricity of the friction shaft is arranged to change position relative to the friction brake and compresses the spring element to increase a friction force on the friction shaft, and slow down rotation of the knee just before full extension is reached, without changing the rest of the swing phase of the knee.

3. The prosthetic knee of claim 2, wherein the spring element comprises at least one disc spring.

4. The prosthetic knee of claim 2, wherein the spring element is connected to the friction pad by a ball and a guide block.

5. The prosthetic knee of claim 2, wherein a friction screw is located within the housing and is arranged for adjusting preloading of the spring element.

6. The prosthetic knee of claim 5, wherein the spring element is connected to the friction pad by a ball and a guide block, the friction shaft is arranged to compress the spring element to change a distance between the friction screw and the guide block.

7. A prosthetic knee, comprising:
   a housing;
   a chassis;
   a plurality of links pivotally connecting the housing to a locking head;
   a rear link connecting to the housing and the chassis;
   a block lock mechanism including a spring loaded tab block preventing movement of the rear link belonging to the plurality of links when it is engaged therewith in flexion position, the tab block arranged to be pulled by the spring as the knee enters into extension and remain retracted so as to disengage from the rear link.

* * * * *